(12) United States Patent
Fujii

(10) Patent No.: US 11,382,648 B2
(45) Date of Patent: Jul. 12, 2022

(54) TREATMENT TOOL

(71) Applicant: OLYMPUS CORPORATION, Tokyo (JP)

(72) Inventor: Masahiro Fujii, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 83 days.

(21) Appl. No.: 16/862,631

(22) Filed: Apr. 30, 2020

(65) Prior Publication Data

US 2020/0253629 A1  Aug. 13, 2020

Related U.S. Application Data

(63) Continuation of application No. PCT/JP2017/039908, filed on Nov. 6, 2017.

(51) Int. Cl.
```
A61B 17/32    (2006.01)
A61B 90/00    (2016.01)
A61B 17/00    (2006.01)
```

(52) U.S. Cl.
CPC .. *A61B 17/32002* (2013.01); *A61B 17/00234* (2013.01); *A61B 90/03* (2016.02); *A61B 2017/0034* (2013.01); *A61B 2090/035* (2016.02)

(58) Field of Classification Search
CPC ........ A61B 17/32002; A61B 17/00234; A61B 90/03; A61B 2090/035; A61B 2017/0034; A61B 2090/034; A61B 17/29
See application file for complete search history.

(56) References Cited

U.S. PATENT DOCUMENTS

2007/0250113 A1* 10/2007 Hegeman ............... H04W 24/08
                                                         606/207
2007/0287993 A1   12/2007 Hinman et al.
2009/0054733 A1    2/2009 Marescaux et al.
(Continued)

FOREIGN PATENT DOCUMENTS

CA    2633245 A1    2/2009
EP    2027820 A1    2/2009
(Continued)

OTHER PUBLICATIONS

International Search Report dated Jan. 23, 2018 issued in International Application No. PCT/JP2017/039908.

*Primary Examiner* — Brooke Nicole Labranche
(74) *Attorney, Agent, or Firm* — Scully, Scott, Murphy & Presser, P.C.

(57) ABSTRACT

A treatment tool includes an long member; a treatment portion rotatable about a longitudinal axis of the long member; a twisting wire one end of which is connected to the treatment portion, the other end extending toward a proximal end side of the long member; an operating portion, at the proximal end side, that includes a body fixed to the long member, and an operating member configured to rotate around and move along the axis; and a mechanism configured to couple the operating member with the wire and convert a rotation of the operating member into traction of the wire. The body includes a portion configured to come into contact with the operating member to prevent the rotation in a case where the operating member is urged in a direction toward a distal end side of the long member together with the mechanism by a restoring force of the wire.

16 Claims, 20 Drawing Sheets

(56) References Cited

U.S. PATENT DOCUMENTS

| | | |
|---|---|---|
| 2015/0141992 A1 | 5/2015 | Smith |
| 2015/0196313 A1 | 7/2015 | Ishida et al. |
| 2018/0078279 A1* | 3/2018 | Germain .......... A61B 17/32002 |
| 2018/0112422 A1 | 4/2018 | Fuji |

FOREIGN PATENT DOCUMENTS

| | | |
|---|---|---|
| EP | 2901956 A1 | 5/2015 |
| JP | S64-026017 U | 2/1989 |
| JP | 2006-326148 A | 12/2006 |
| JP | 2009-050697 A | 3/2009 |
| JP | 2009-539567 A | 11/2009 |
| JP | 6042678 B | 12/2016 |
| JP | 2017-500092 A1 | 1/2017 |
| WO | 2007/146894 A2 | 12/2007 |
| WO | 2015/077350 A1 | 5/2015 |
| WO | 2018/073951 A1 | 4/2018 |

* cited by examiner

TREATMENT TOOL

CROSS-REFERENCE TO RELATED APPLICATIONS

This is a continuation of International Application PCT/JP2017/039908 which is hereby incorporated by reference herein in its entirety.

TECHNICAL FIELD

The present invention relates to a treatment tool.

BACKGROUND ART

To date, there is a known treatment tool in which an end effector such as a gripper disposed at a distal end of an elongated insertion portion is pivoted by a manual operating portion disposed at a proximal end of the insertion portion (for example, see PTL 1).

This treatment tool includes a brake rotor that, even if an inclined end effector receives a reaction force from living tissue, rotates in conjunction with the rotation of the operating portion so that the inclination does not change due to the reaction force, a brake shoe that can move forward and backward with respect to the brake rotor, and an elastic member that urges the brake shoe in a direction in which the brake shoe is pressed against the brake rotor.

CITATION LIST

Patent Literature

{PTL 1} Publication of Japanese Patent No. 6042678

SUMMARY OF INVENTION

According to an aspect of the present invention, a treatment tool includes an elongated long member; a treatment portion supported at a distal end of the long member so as to be rotatable about a longitudinal axis of the long member; a twisting wire one end of which is connected to the treatment portion, the other end of the twisting wire extending toward a proximal end side of the long member through an inside of the long member; an operating portion disposed at the proximal end side of the long member, the operating portion including an operating portion body fixed to the long member, and a movable operating member configured to, by an operation of an operator, rotate around the longitudinal axis of the long member and move along the longitudinal axis; and a converting mechanism configured to couple the movable operating member with the twisting wire and convert a rotation of the movable operating member into traction of the twisting wire, wherein the operating portion body includes a contact portion configured to come into contact with the movable operating member to prevent the rotation of the movable operating member in a case where the movable operating member is urged in a direction toward a distal end side of the long member together with the converting mechanism by a restoring force of the twisting wire.

DESCRIPTION OF EMBODIMENTS

A treatment tool 1 according to an embodiment of the present invention will be described below with reference to the drawings.

Figure 1:
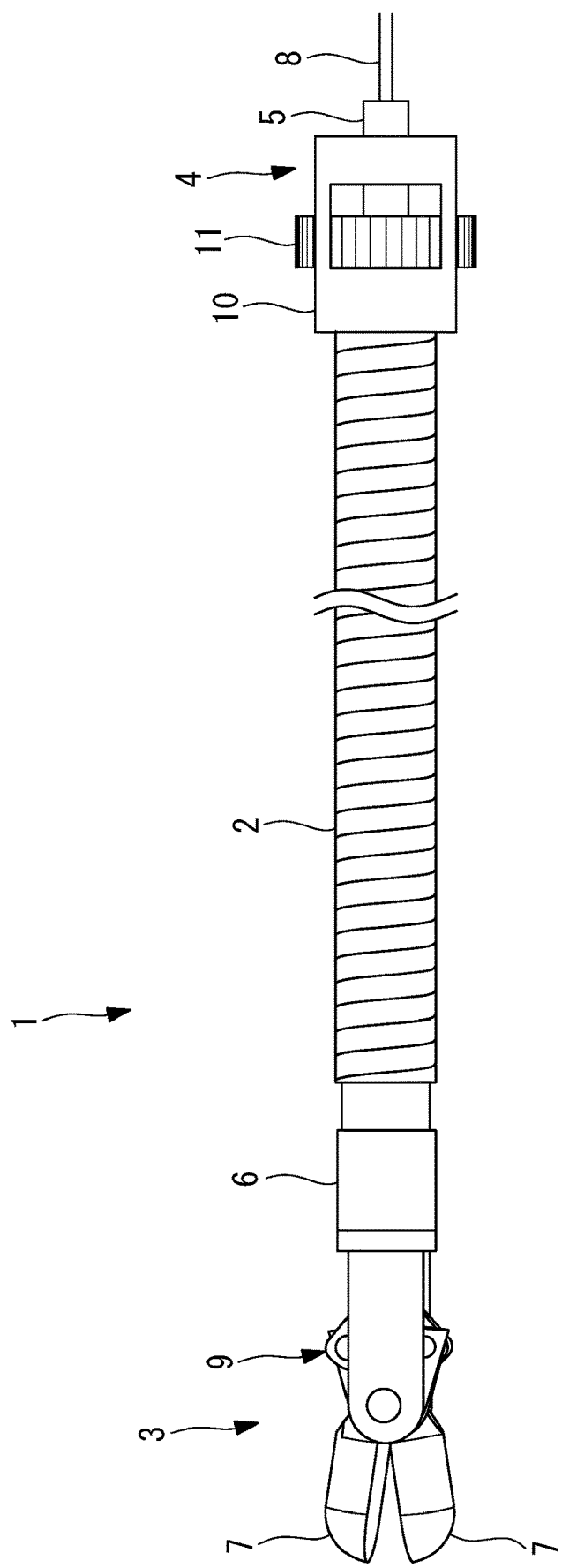
FIG. 1 is an overall configuration diagram illustrating a treatment tool according to an embodiment of the present invention.
Figure 3:
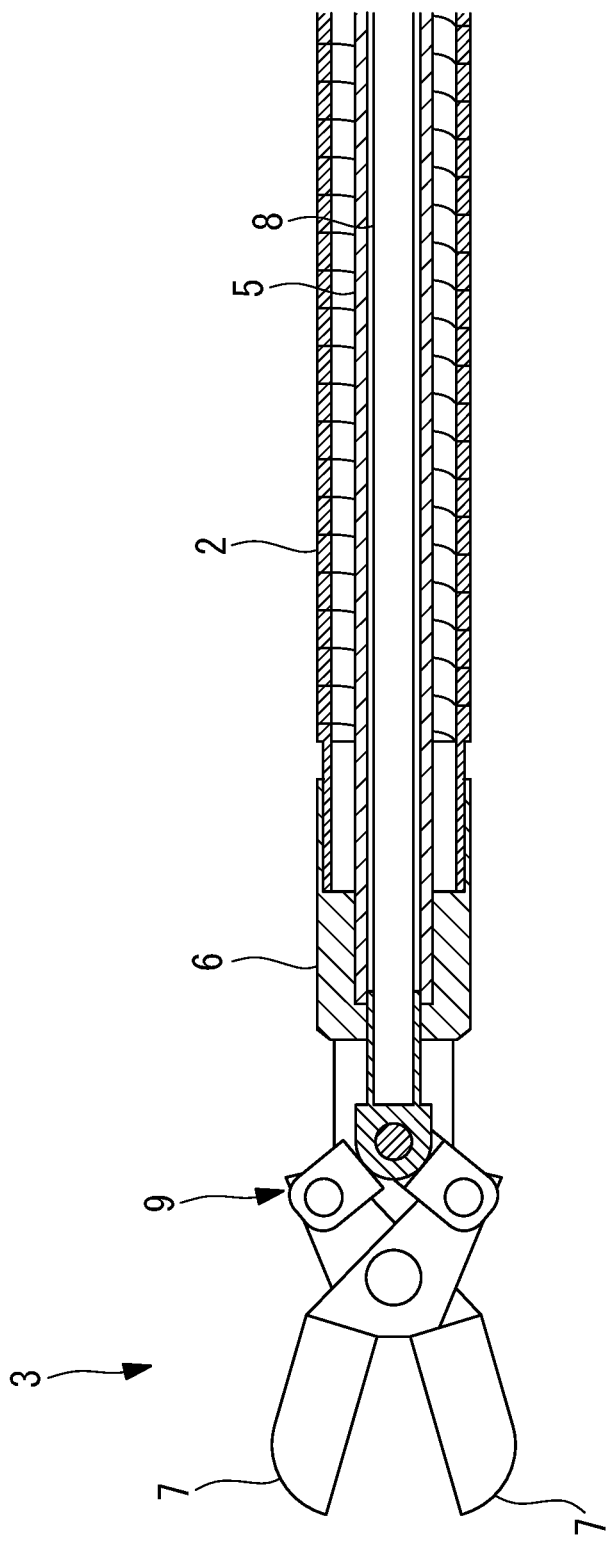
FIG. 3 is a longitudinal sectional view of a distal end portion of the treatment tool in FIG. 1.

As illustrated in FIGS. 1 and 3, the treatment tool 1 according to the present embodiment includes an elongated soft tubular coil sheath (long member) 2, a gripper (treatment portion) 3 supported at a distal end of the coil sheath 2 so as to be rotatable about a longitudinal axis of the coil sheath 2, an operating portion 4 disposed at a proximal end of the coil sheath 2, and a soft tubular twisting wire (motive-force transmission member) 5 one end of which is connected to the gripper 3. The other end of the twisting wire 5 extends toward a proximal end side of the coil sheath 2 through an inside of the coil sheath 2.

The gripper 3 includes a rotation member 6 supported at the distal end of the coil sheath 2 so as to be rotatable about the longitudinal axis of the coil sheath 2, a pair of gripping pieces 7 that, by being attached to the rotation member 6 so as to be pivotable about an axis perpendicular to the longitudinal axis, have distal ends that can be opened and closed, and a link mechanism 9 disposed between a distal end of a wire 8, which penetrates through the twisting wire 5 and is guided from a proximal end side, and the gripping piece 7.

Figure 2:
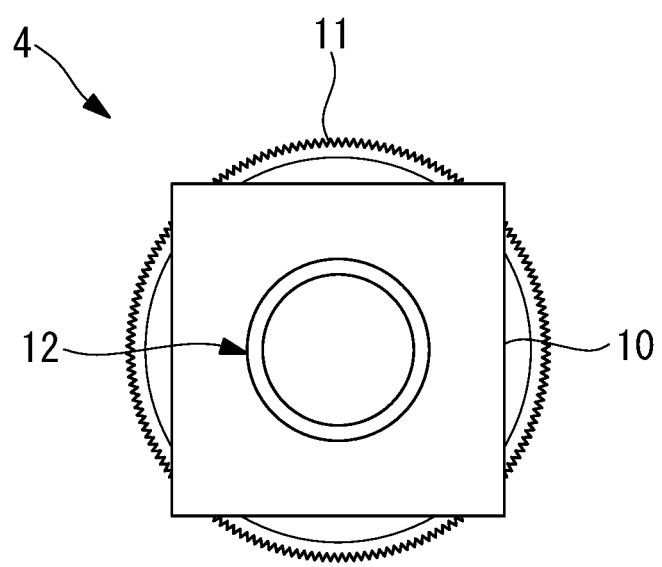
FIG. 2 is a front view illustrating an operating portion of the treatment tool in FIG. 1.
Figure 4:
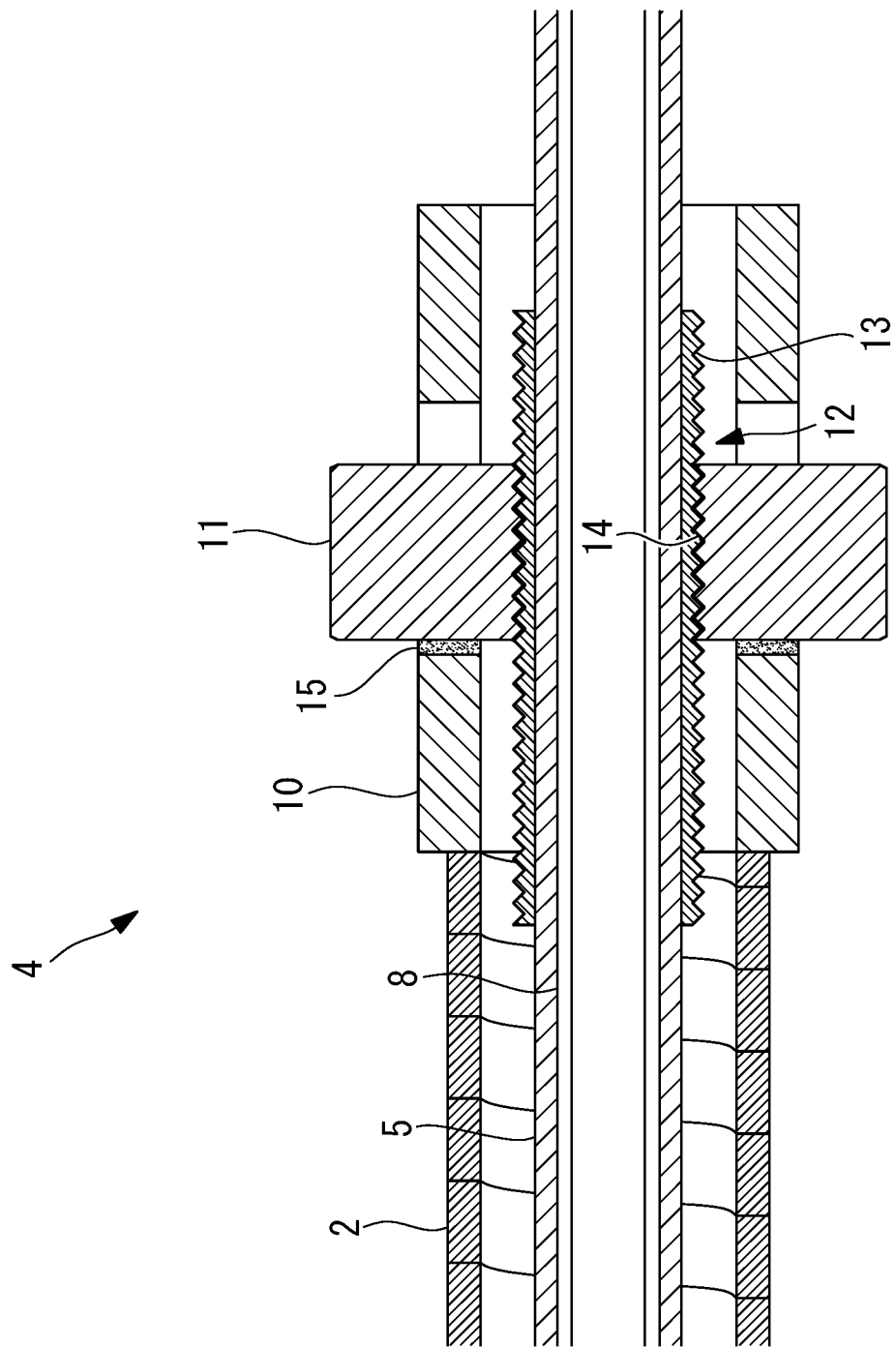
FIG. 4 is a longitudinal sectional view illustrating a state in which a dial of the operating portion in FIG. 2 is advanced.

As illustrated in FIGS. 2 and 4, the operating portion 4 includes an operating portion body 10 fixed to the proximal end of the coil sheath 2, a dial (movable operating member) 11 supported with respect to the operating portion body 10 so as to be rotatable about the longitudinal axis of the coil sheath 2, and a converting mechanism 12 that is disposed between the dial 11 and the twisting wire 5 and that couples the dial 11 with the twisting wire 5. The converting mechanism 12 converts rotation of the dial 11 into traction in the longitudinal axis direction of the twisting wire 5. The converting mechanism 12 includes, for example, a male thread 13 fixed to a portion of the twisting wire 5 in the longitudinal axis direction, and a female thread 14 fixed to the dial 11 and fastened to the male thread 13.

In addition, the dial 11 is provided so as to be movable in the longitudinal axis direction of the coil sheath 2 with respect to the operating portion body 10, and, as illustrated in FIG. 4, a contact portion (connection portion) 15 that is brought into contact with the dial 11 at a position where the dial 11 has been moved forward in the longitudinal axis direction, and that locks the dial 11 so as not to rotate about the longitudinal axis with respect to the operating portion body 10 by means of friction at the contact position is provided between the dial 11 and the operating portion body 10. Here, the term "lock" means that the rotation of the dial 11 is prevented.

The operation of the thus-configured treatment tool 1 according to the present embodiment will be described.

In order to perform treatment of an affected site using the treatment tool 1 according to the present embodiment, while ensuring a sufficiently large visual field with an endoscope or the like, the treatment tool 1 is inserted into a body from a distal end of the insertion portion of the endoscope while facing the affected site. In this state, the rotation member 6 is rotated about the longitudinal axis at the distal end of the coil sheath 2 to adjust the angle of the gripper 3 about the longitudinal axis.

Figure 5:
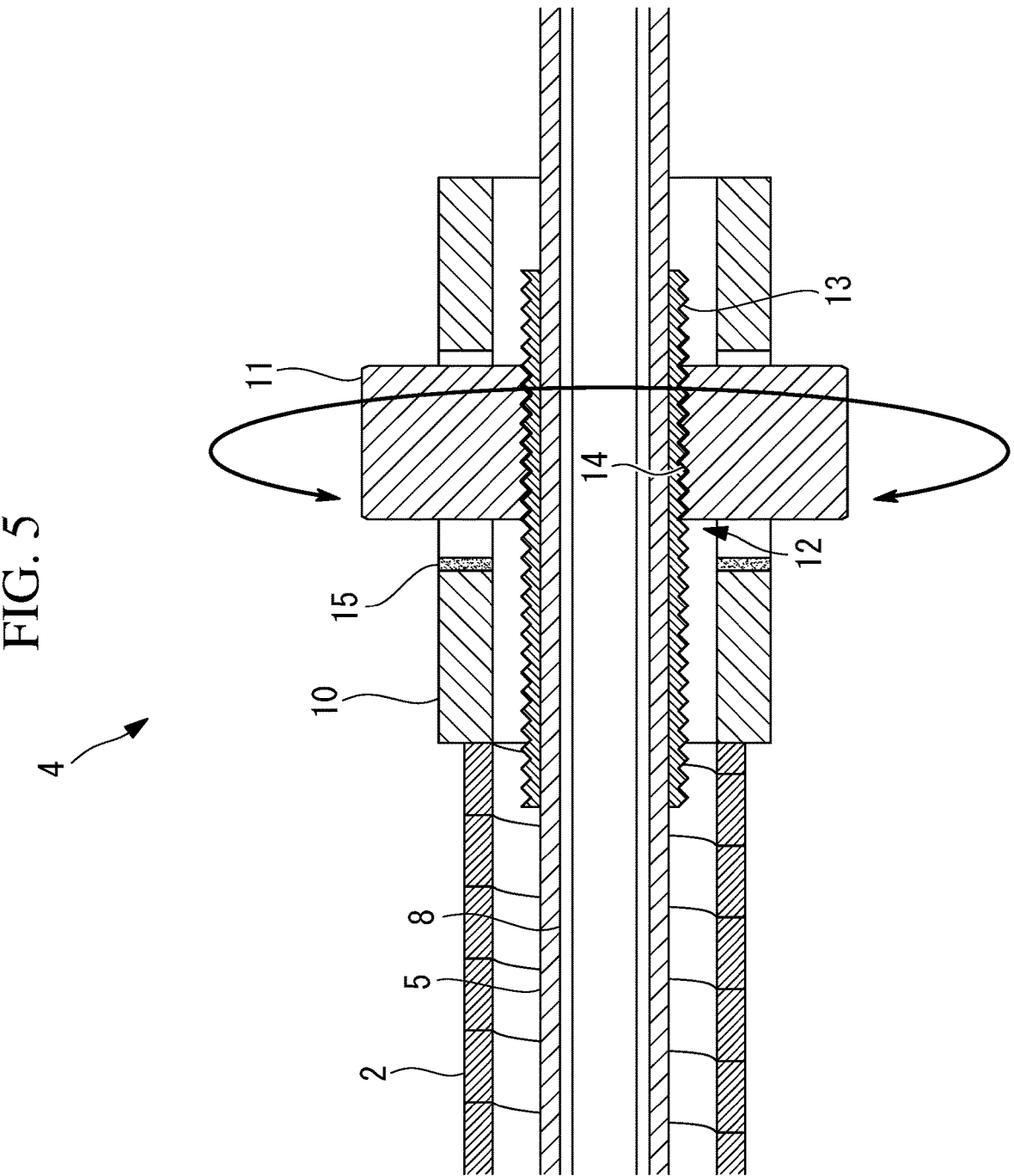
FIG. 5 is a longitudinal sectional view illustrating a state in which the dial of the operating portion in FIG. 2 is retracted.

At this time, as illustrated in FIG. 5, the operator slightly moves the dial 11 with respect to the operating portion body 10 of the operating portion 4 rearward in the longitudinal axis direction of the coil sheath 2. Consequently, because the dial 11 becomes separated from the contact portion 15, and the frictional resistance between the contact portion 15 and the dial 11 disappears, the operator can easily rotate the dial 11 about the longitudinal axis with respect to the operating portion body 10.

The converting mechanism 12 is disposed between the dial 11 and the twisting wire 5 and couples the dial 11 with the twisting wire 5. The converting mechanism 12 converts the rotational force of the dial 11 input by the operator into tension of the twisting wire 5. The twisting wire 5 converts the tension applied to a proximal end of the twisting wire 5 along the longitudinal axis direction into a rotational force about the longitudinal axis at a distal end of the twisting wire 5. In other words, twisting wire 5 rotates around the longitudinal axis of the elongated soft tubular coil sheath (long member) 2 in response to the traction in a direction of the longitudinal axis of the long member 2. Consequently, the rotation member 6 fixed to the distal end of the twisting wire 5 is rotated around the longitudinal axis with respect to the coil sheath 2, and the gripper 3 attached to the rotation member 6 is rotated about the longitudinal axis.

Then, with the gripper 3 rotated to a desired angle position, when a hand of the operator is released, the dial 11 is pulled together with the converting mechanism 12 forward in the longitudinal axis direction and is brought into contact with the contact portion 15 by restoring force of the twisting wire 5. In this case, the relative movement of the dial 11 with respect to the operating portion body 10 is locked by the frictional resistance generated between the dial 11 and the contact portion 15.

In this way, in the treatment tool 1 according to the present embodiment, the dial 11 is urged to be brought into contact with the contact portion 15 by restoring force of the twisting wire 5 when the dial 11 is not operated by the operator. In this case, the dial 11 does not rotate with respect to the operating portion body 10 by the frictional resistance generated between the dial 11 and the contact portion 15. When rotating the gripper 3, the friction force disappears just by slightly moving the dial 11 rearward in the longitudinal axis direction with respect to the operating portion body 10, thereby making it possible to easily switch to a state in which rotation of the dial 11 with respect to the operating portion body 10 is permitted. As a result, there is an advantage that a compact operating portion 4 can be formed with a small number of components without employing a large-scale mechanism such as one using a conventional brake rotor and a brake shoe.

In addition, in the present embodiment, since the twisting wire 5 that converts the tension input at the proximal end into the rotational force of the rotation member 6 at the distal end is employed as the motive-force transmission member, the gripper 3 can be rotated with a simple configuration. Since the direction of approach and separation of the dial 11 and the operating portion body 10 at the contact portion 15 matches the direction of input of tension to the twisting wire 5, the dial 11 is urged by the tension (restoring force) of the twisting wire 5 in a direction approaching the contact portion 15, and there is an advantage that the dial 11 can be brought into contact with the operating portion body 10 and locked so as not to rotate simply by the operator releasing his/her hand from the dial 11 after the rotation of the gripper 3 is completed.

Figure 6:
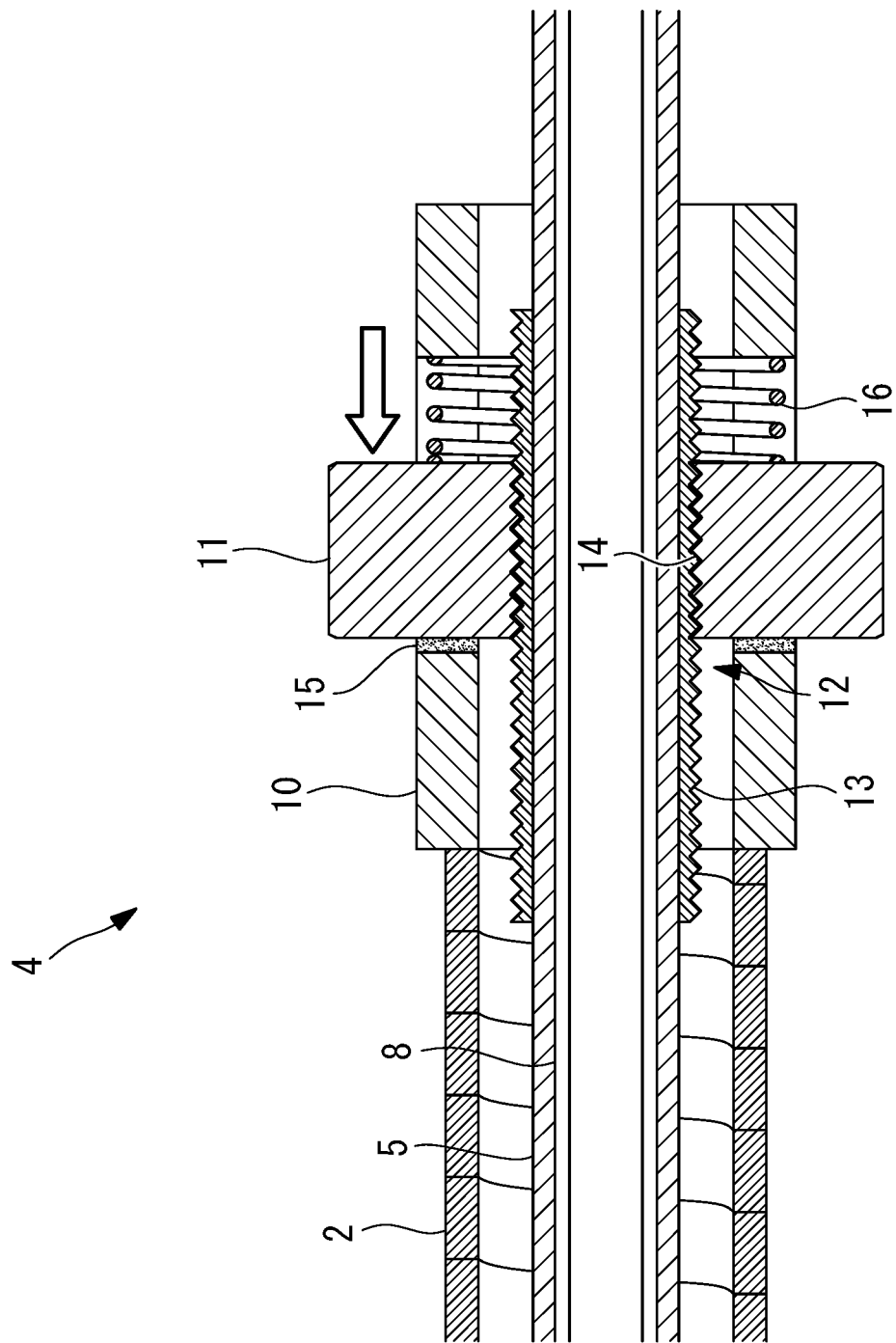
FIG. 6 is a longitudinal sectional view illustrating a first modification of the operating portion in FIG. 2.

Further, in the present embodiment, the dial 11 is urged by the elastic force of the twisting wire 5 in a direction where the contact portion 15 between the dial 11 and the operating portion body 10 is brought into contact the dial 11; however, in addition to this, as illustrated in FIG. 6, an elastic member (urging means) such as a spring 16 or a rubber member that urges the dial 11 in a direction so as to contact the contact portion 15 may be disposed.

Figure 7:
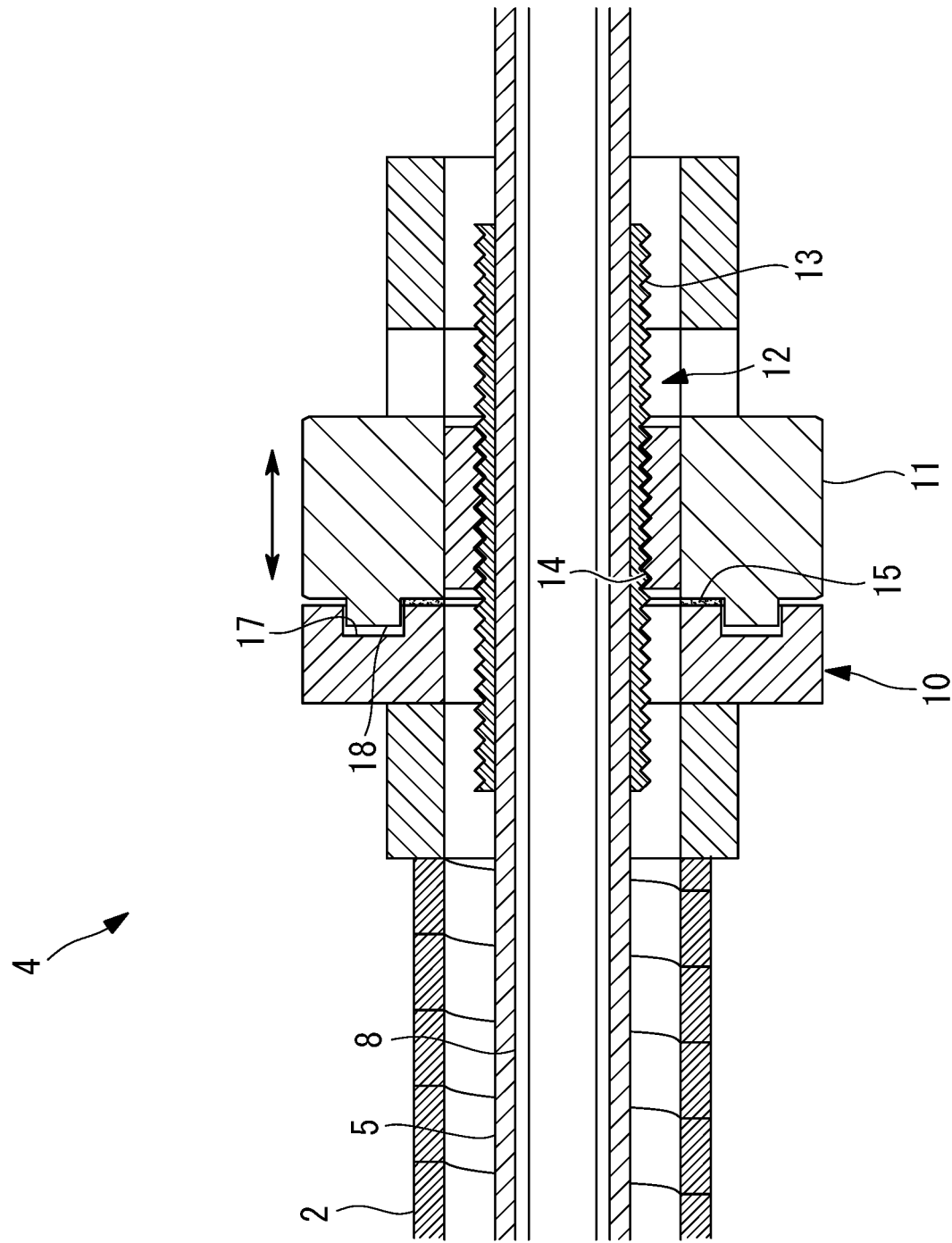
FIG. 7 is a longitudinal sectional view illustrating a second modification of the operating portion in FIG. 2.

In addition, as the contact portion 15 that increases the frictional resistance between the dial 11 and the operating portion body 10, a member having a large friction coefficient such as a rubber member may be disposed, or processing for increasing the surface roughness to increase the coefficient of friction may be performed. In addition, as illustrated in FIG. 7, the dial 11 and the operating portion body 10 may be provided with gears or irregularities 17, 18 that mesh with each other.

Figure 8:
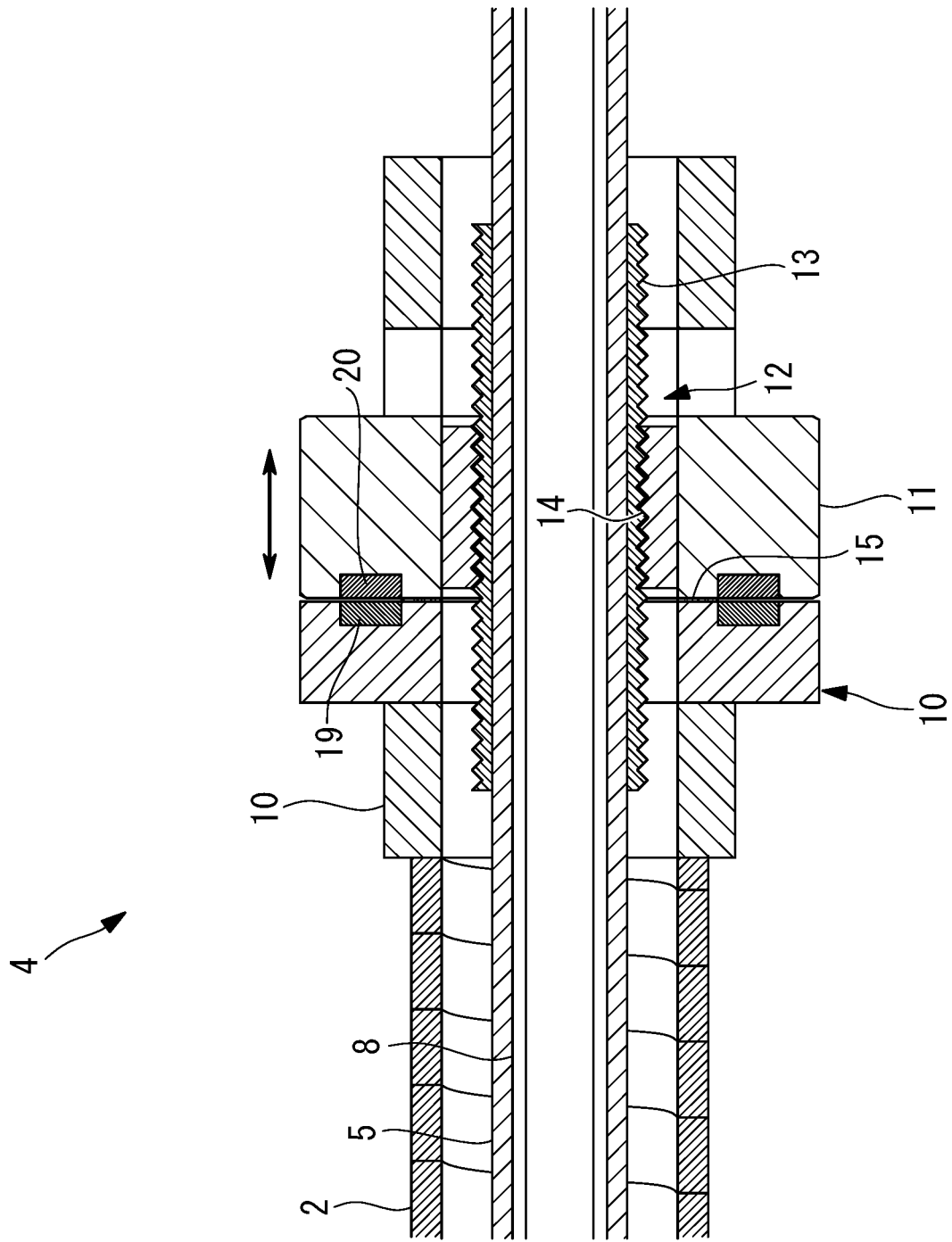
FIG. 8 is a longitudinal sectional view illustrating a third modification of the operating portion in FIG. 2.

In addition, as illustrated in FIG. 8, a magnet (urging means, magnetic member) 19 may be disposed on at least one of the dial 11 and the operating portion body 10, a magnetic member (urging means) 20 may be disposed on the other of the dial 11 and the operating portion body 10, and magnetic attraction force may be used to lock the dial 11 and the operating portion body 10 in a state in which the dial 11 and the operating portion body 10 are brought close to each other. In addition, instead of the spring 16 in FIG. 6, magnetic members 20 having the same polarity may be disposed, and the dial 11 may be urged by a magnetic repulsive force in a direction where the contact portion 15 between the dial 11 and the operating portion body 10 is brought into contact with the dial 11.

Figure 9:
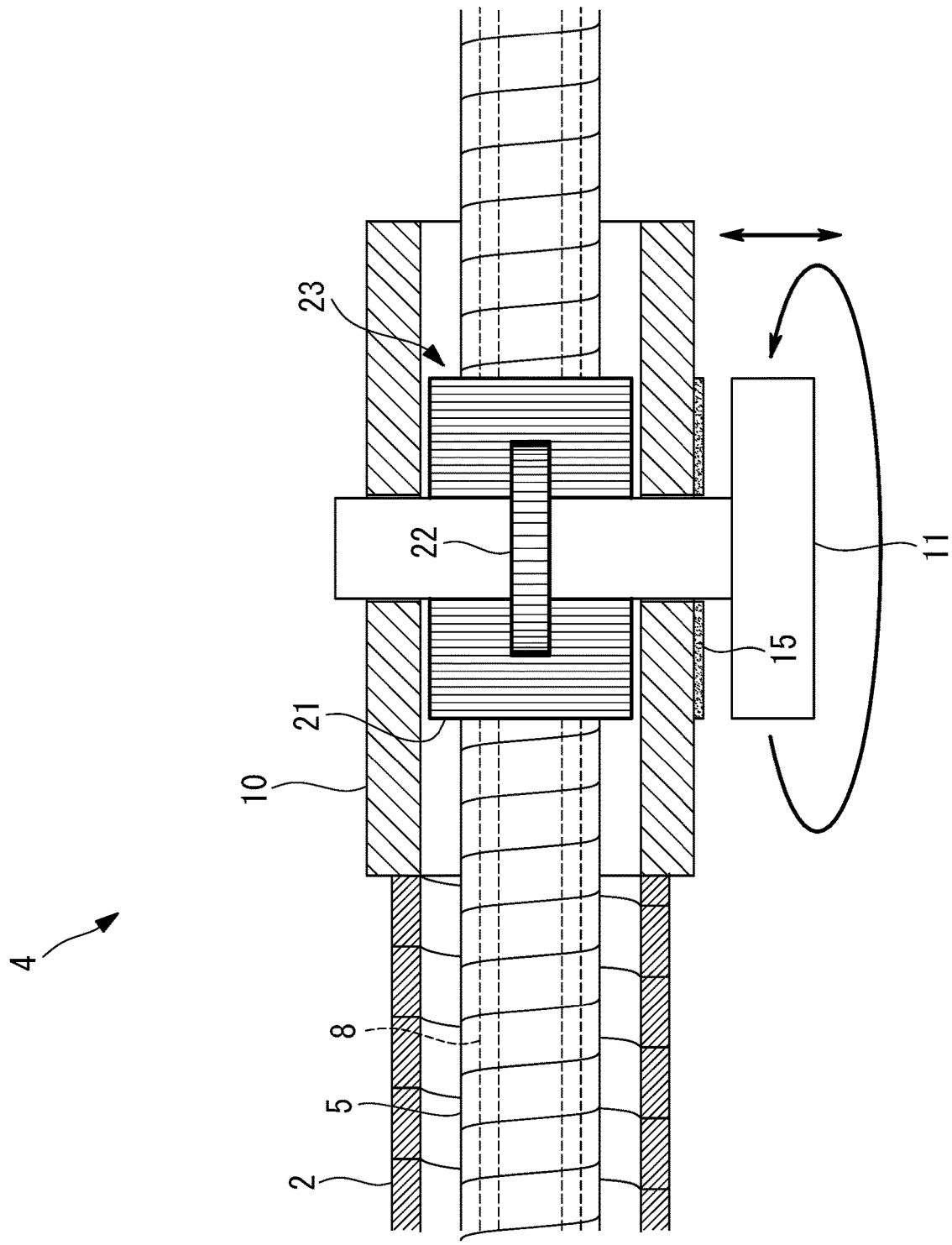
FIG. 9 is a longitudinal sectional view illustrating a fourth modification of the operating portion in FIG. 2.

In addition, in the present embodiment, the rotation of the dial 11 is converted into tension input to the twisting wire 5 by the converting mechanism 12, but instead of this, as illustrated in FIG. 9, a gear mechanism 23 including a rack gear 21 fixed to the twisting wire 5 and a pinion gear 22 fixed to the dial 11 may be adopted. In this case, the dial 11 is disposed so as to be rotatable about a rotation axis that is disposed in skew alignment with the longitudinal axis of the twisting wire 5, and the rack gear 21 and the pinion gear 22 are provided so as to be movable along the rotation axis while maintaining an engaged state.

Thus, when rotating the dial 11, the contact portion 15 between the dial 11 and the operating portion body 10 is separated from the dial 11 by moving the dial 11 along the axis. In this state, because the frictional resistance between the dial 11 and the operating portion body 10 disappears, the dial 11 can be easily rotated with respect to the operating portion body 10, and the rotation of the pinion gear 22 causes the rack gear 21 to linearly move in one direction to generate tension in the twisting wire 5. On the other hand, when ending the dial operation, the dial 11 is moved along the axis such that the contact portion 15 between the dial 11 and the operating portion body 10 is brought into contact with the dial 11. As a result, the frictional resistance between the dial 11 and the operating portion body 10 increases, and the dial 11 is locked so as not to rotate with respect to the operating portion body 10.

Figure 10:
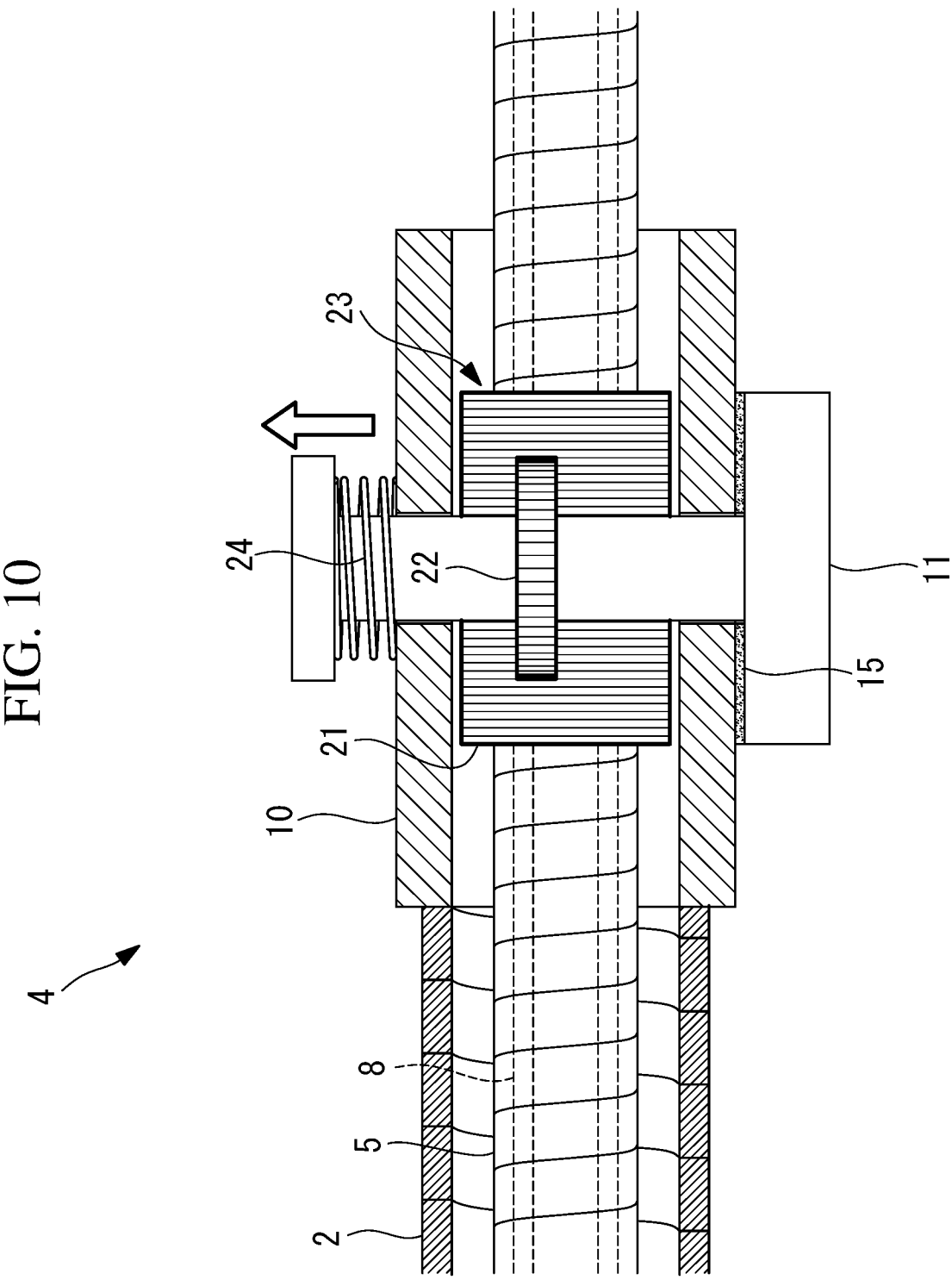
FIG. 10 is a longitudinal sectional view illustrating a modification of the operating portion in FIG. 9.

In addition, also in this case, as illustrated in FIG. 10, an elastic member such as a spring (urging means) 24 or a rubber member that urges the dial 11 in a direction where the contact portion 15 between the dial 11 and the operating portion body 10 is brought into contact with the dial 11 may be used.

In addition, in the present embodiment, the rotation of the dial 11 is converted into tension input to the twisting wire 5 by the converting mechanism 12; however, instead of this, an operation piece (movable operating member) 25 fixed to the twisting wire 5 may be disposed on a portion of the twisting wire 5 in the longitudinal axis direction, and by moving the operation piece 25 with respect to the operating portion body 10 in the longitudinal axis direction of the twisting wire 5, tension input to the twisting wire 5 may be directly generated.

Figure 11:
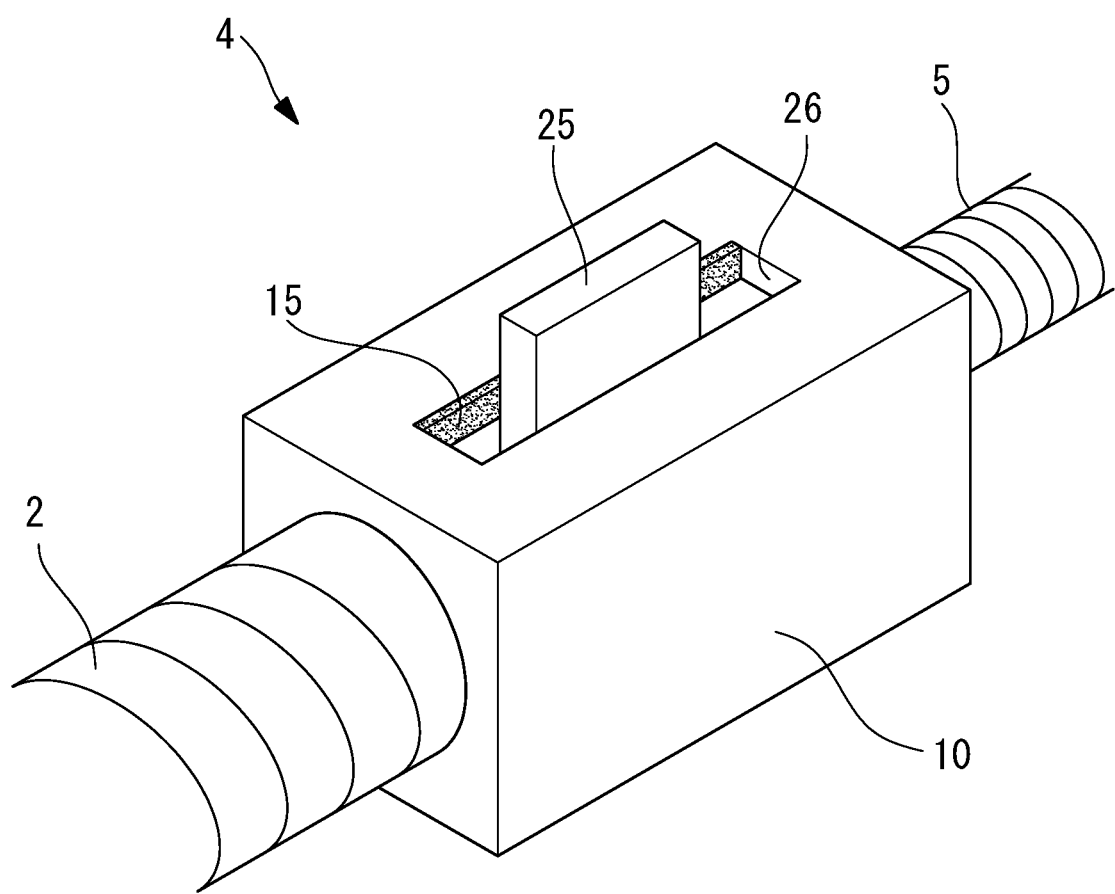
FIG. 11 is a perspective view illustrating a fifth modification of the operating portion in FIG. 2.
Figure 12:
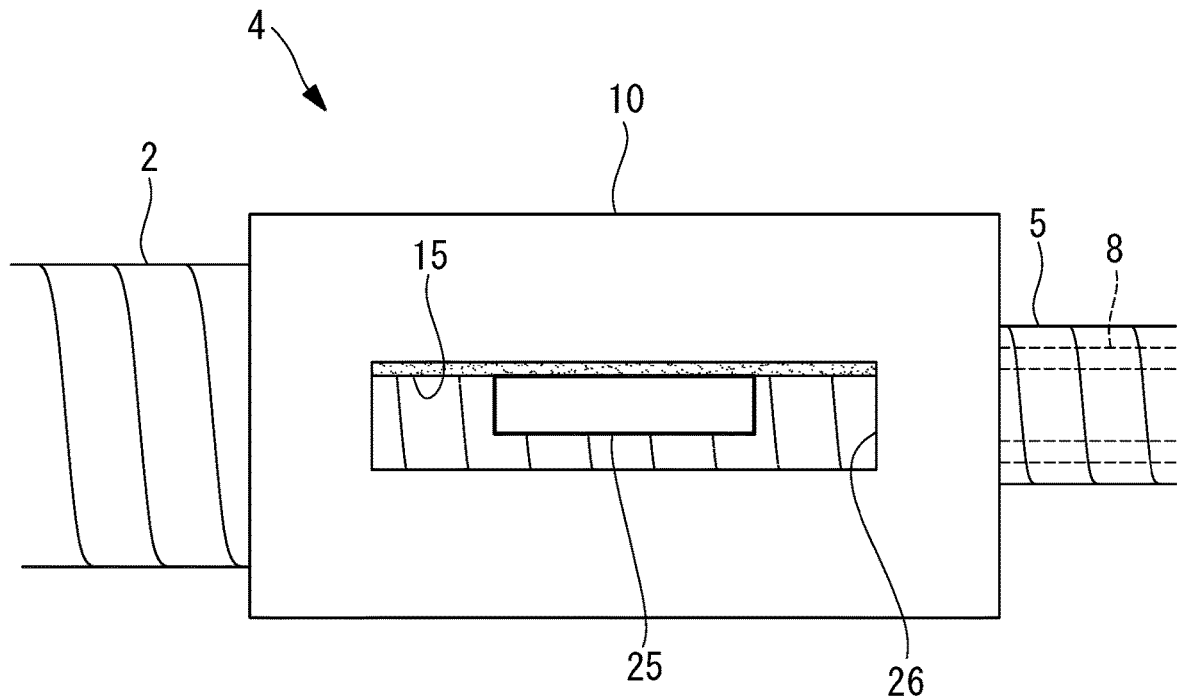
FIG. 12 is a side view illustrating a state in which an operation piece of the operating portion in FIG. 11 and an operating portion body are brought into contact with each other at a contact portion.
Figure 13:
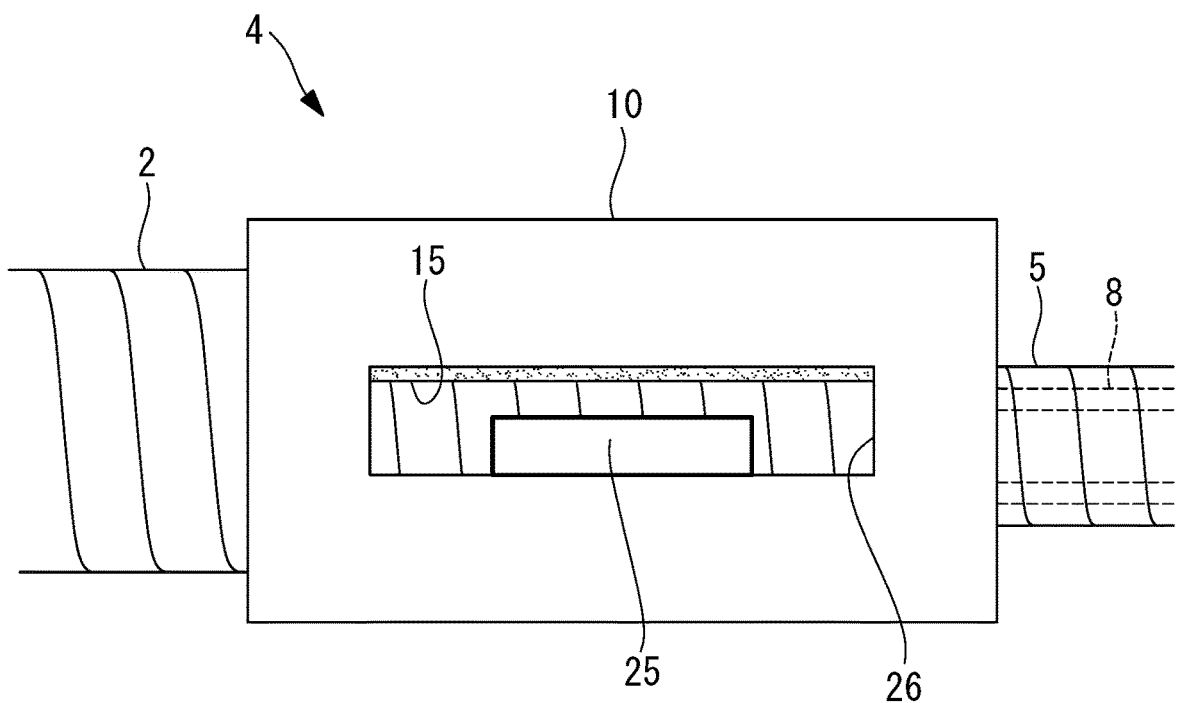
FIG. 13 is a side view illustrating a state in which the operation piece of the operating portion and the operating portion body in FIG. 11 are separated from each other at the contact portion.

In this case, as illustrated in FIG. 11, a slit 26 for movably disposing the operation piece 25 is provided in the operating portion body 10, the width dimension of the slit 26 is made sufficiently larger than the width dimension of the operation piece 25 to enable the operation piece 25 to move in the width direction in the slit 26, and, as illustrated in FIG. 12 and FIG. 13, the contact portion 15 may be provided on an inner wall on one side in the width direction of the slit 26, the contact portion 15 having been subjected to processing for generating a large frictional resistance when it comes into contact with the operation piece 25.

When the operation piece 25 is moved with respect to the operating portion body 10, as illustrated in FIG. 13, the operation piece 25 is moved in the width direction in the slit 26 so as to separate the contact portion 15 from the operation piece 25. On the other hand, when the operation piece 25 is to be locked with respect to the operating portion body 10, the operation piece 25 is moved in the width direction in the slit 26 so as to bring the contact portion 15 into contact with the operation piece 25, as illustrated in FIG. 12.

Figure 14:
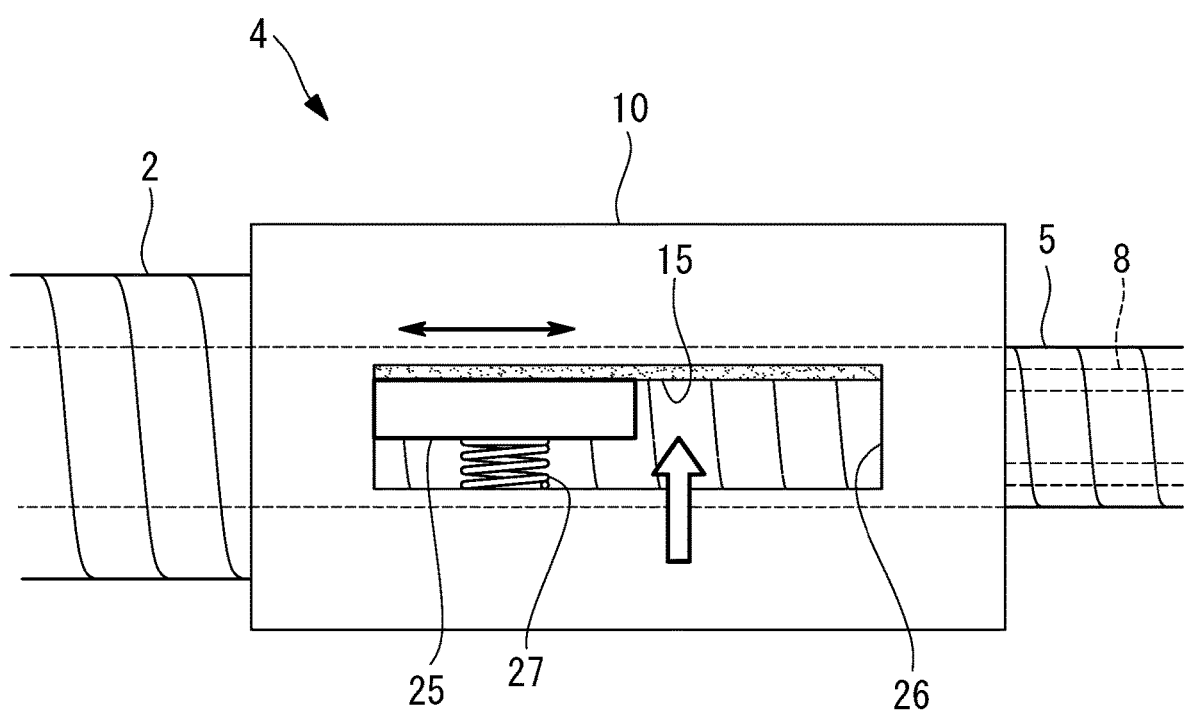
FIG. 14 is a side view illustrating a modification of the operating portion in FIG. 11.

Further, as illustrated in FIG. 14, an elastic member such as a spring (urging means) 27 or a rubber member, which urges the operation piece 25 in the width direction in the slit 26 and in a direction to contact the contact portion 15, is provided.

Figure 15:
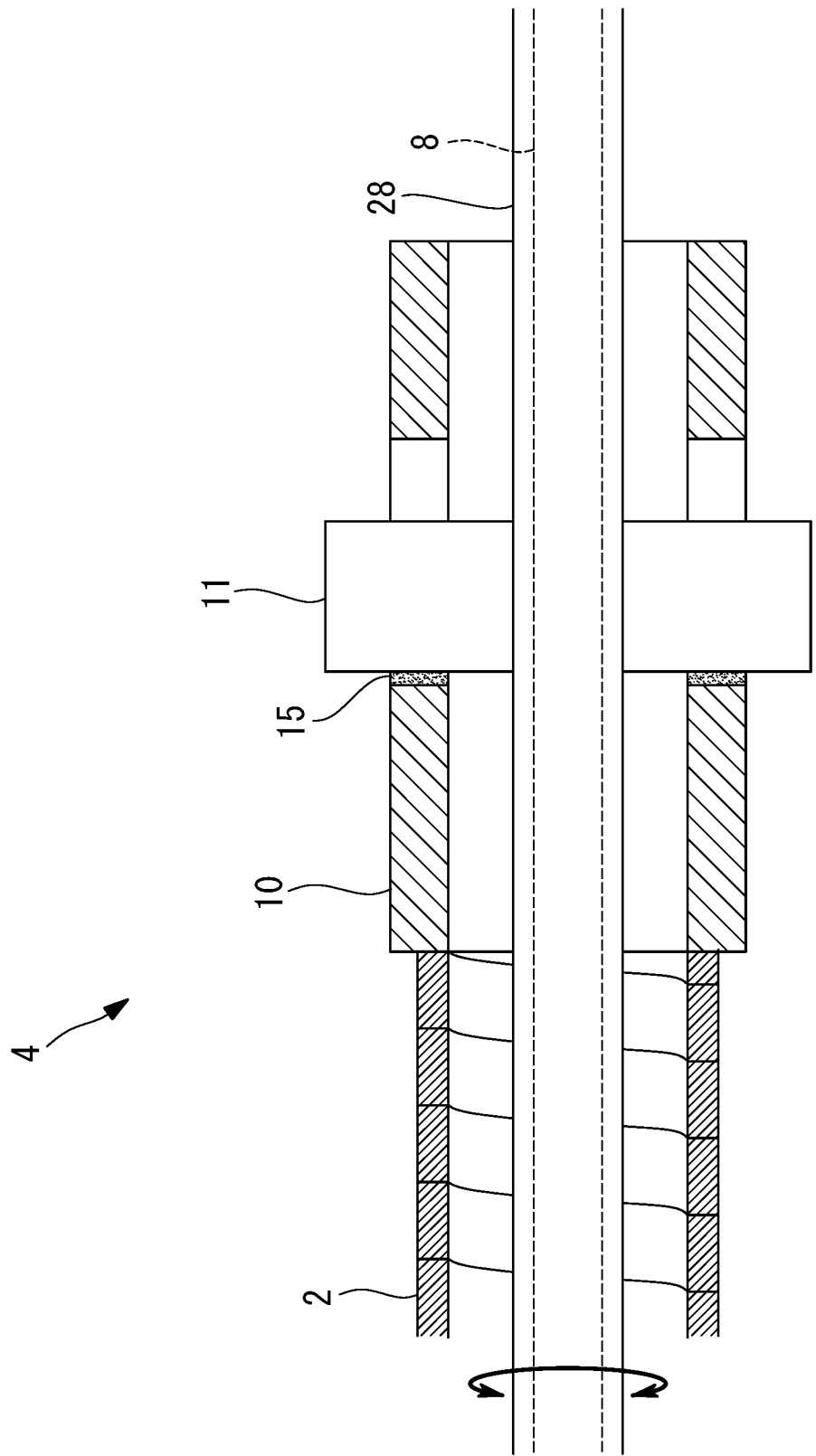
FIG. 15 is a partial vertical sectional view of the vicinity of the operating portion illustrating a modification of the treatment tool in FIG. 1.
Figure 16:
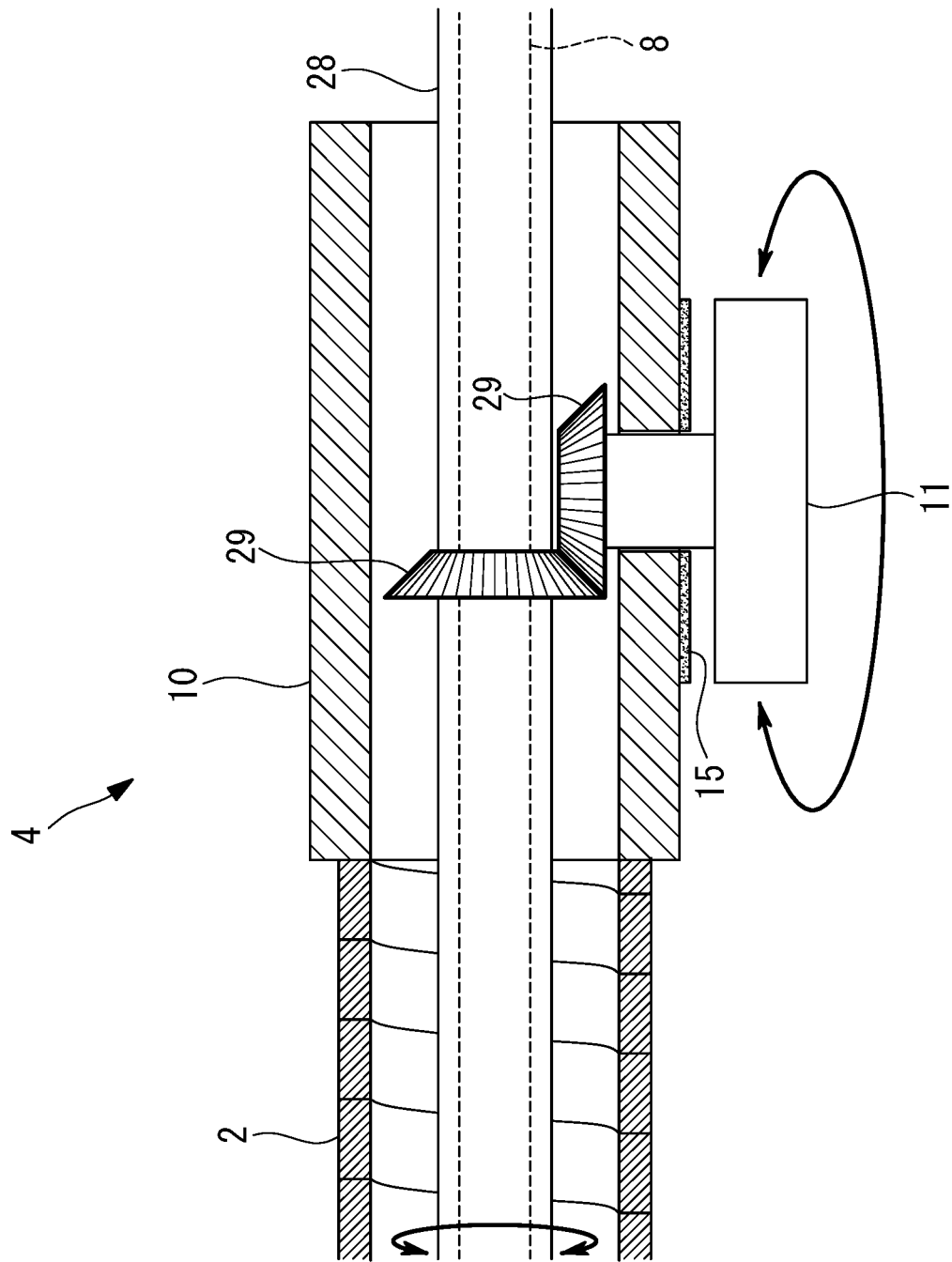
FIG. 16 is a partial vertical sectional view of the vicinity of the operating portion illustrating a modification of the treatment tool in FIG. 15.

In addition, in the present embodiment, as the motive-force transmission member, the twisting wire 5 that converts tension into a rotational force and rotates the gripper 3 about the longitudinal axis is employed; however, instead of this, as illustrated in FIGS. 15 and 16, a torque tube or a shaft 28 that transmits the input rotational force may be employed. The connection between the dial 11 and the shaft 28 illustrated in FIG. 15 may be established using a connection method in which the relative rotation about the longitudinal axis of the shaft 28 is locked and relative movement along the longitudinal axis is enabled. The connection method may be performed using, for example, a key and a key groove, or a spline gear.

In addition, as illustrated in FIG. 16, when transmitting the rotational force from the dial 11, which is supported so as to be rotatable about an axis perpendicular to the longitudinal axis of the shaft 28, to the shaft 28 by a bevel gear 29, the bevel gear 29 and the dial 11 may be connected movably in a direction along the rotation axis of the dial 11 while maintaining the engagement of the bevel gear 29. The connection method may be the same as described above.

Figure 17:
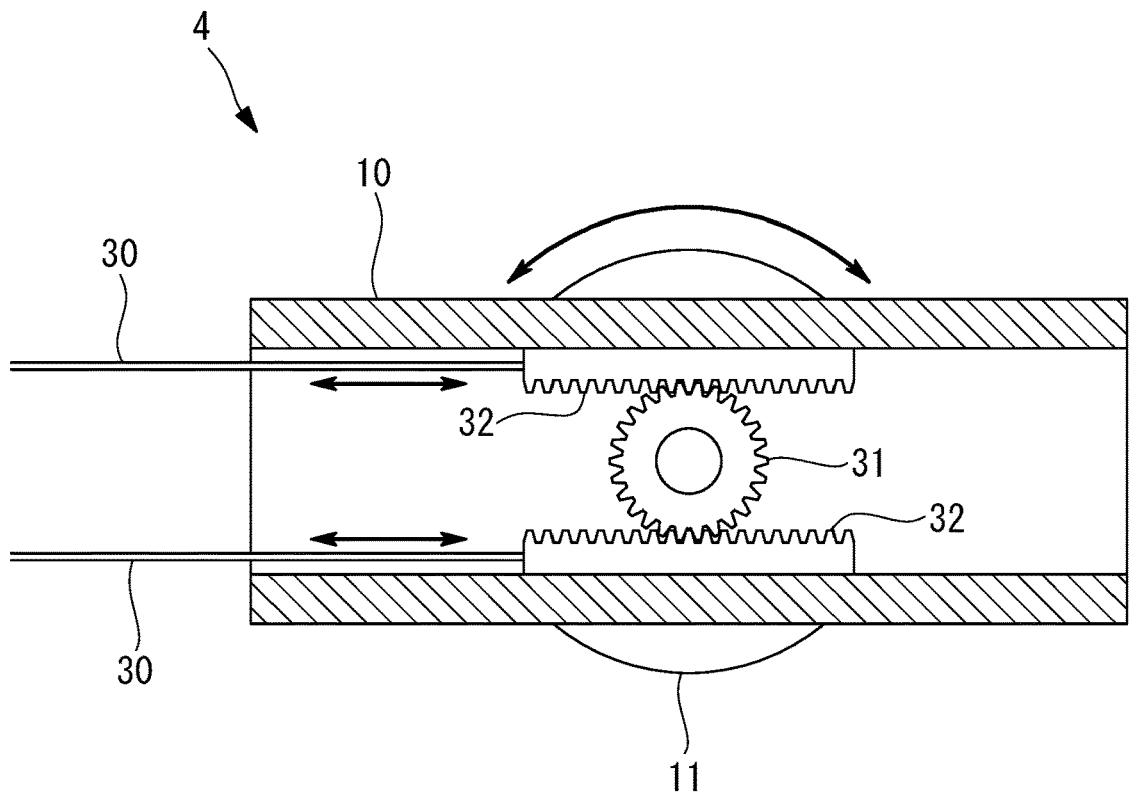
FIG. 17 is a partial vertical sectional view of the vicinity of the operating portion illustrating another modification of the treatment tool in FIG. 1.
Figure 18:
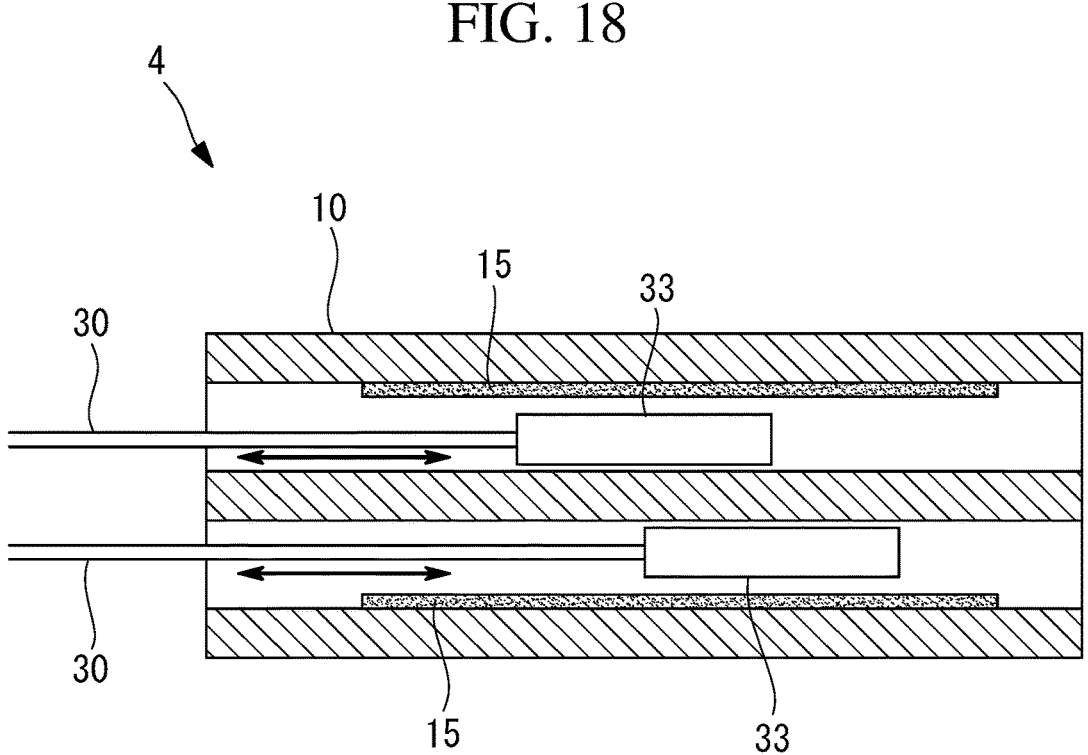
FIG. 18 is a partial vertical sectional view of the vicinity of the operating portion illustrating a modification of the treatment tool in FIG. 17.

In addition, as illustrated in FIGS. 17 and 18, wires 30 may be employed as motive-force transmission members. In the case in FIG. 17, for example, it suffices to include a pinion gear 31 that fixes the rotational force of the dial 11 to the dial 11, and rack gears 32 that are fixed to each of the two wires 30 and engage with the pinion gear 31 on both sides of the pinion gear 31. In addition, in this case, the rotation member 6 rotatably supported at the distal end of the coil sheath 2 may be provided with a conversion mechanism (not illustrated) that converts the tension of the wires 30 into a rotational force.

In the case in FIG. 18, tension can be applied to the wires 30 by moving operation pieces (movable operating members) 33 fixed to the wires 30 with respect to the operating portion body 10 in the longitudinal axis direction of the wires 30.

Figure 19:
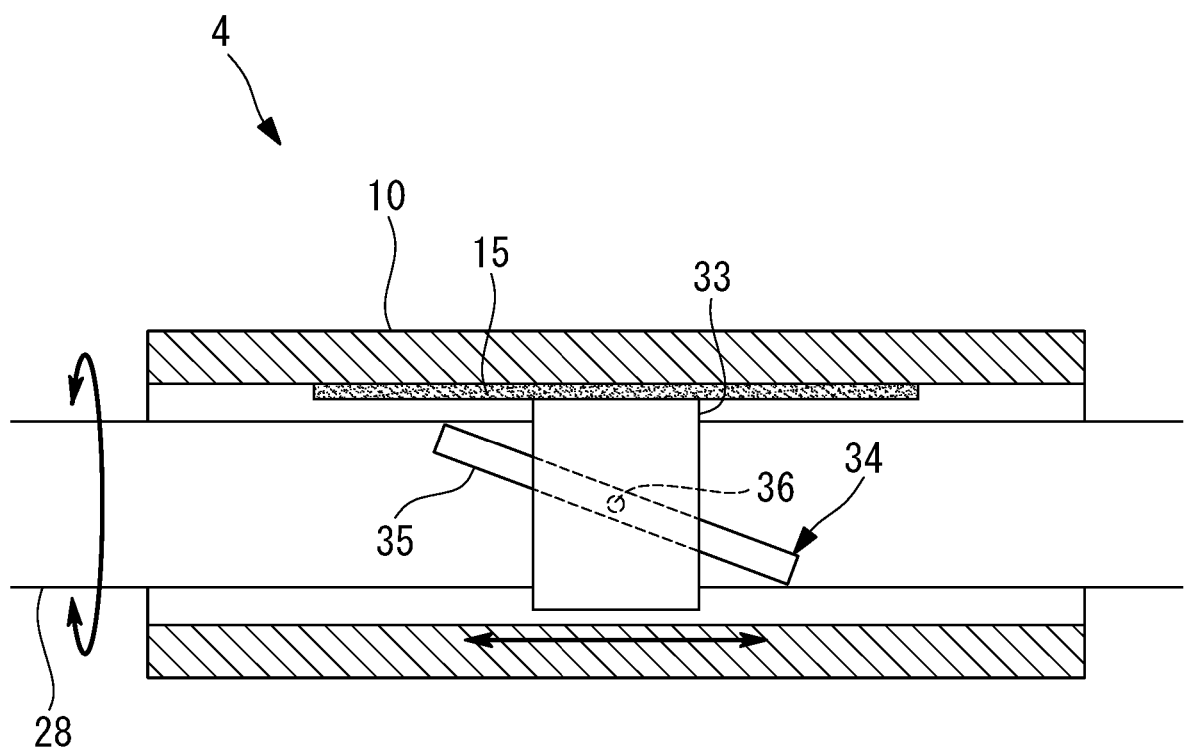
FIG. 19 is a partial vertical sectional view of the vicinity of the operating portion illustrating another modification of the treatment tool in FIG. 1.

In addition, as illustrated in FIG. 19, a cam mechanism 34 may be employed as a mechanism for converting the linear movement of the operation piece 33 along the longitudinal axis direction of the shaft 28 into a rotation operation about the longitudinal axis of the shaft 28. In the example illustrated in FIG. 19, the cam mechanism 34 includes a cam groove 35 helically extending along the outer peripheral surface of the shaft 28, and a pin 36 provided in the operation piece 33 and engaging with the cam groove 35.

When the operation piece 33 is moved in the longitudinal axis direction of the shaft 28, the pin 36 moves in the cam groove 35, and, consequently, the shaft 28 is rotated.

Figure 20:
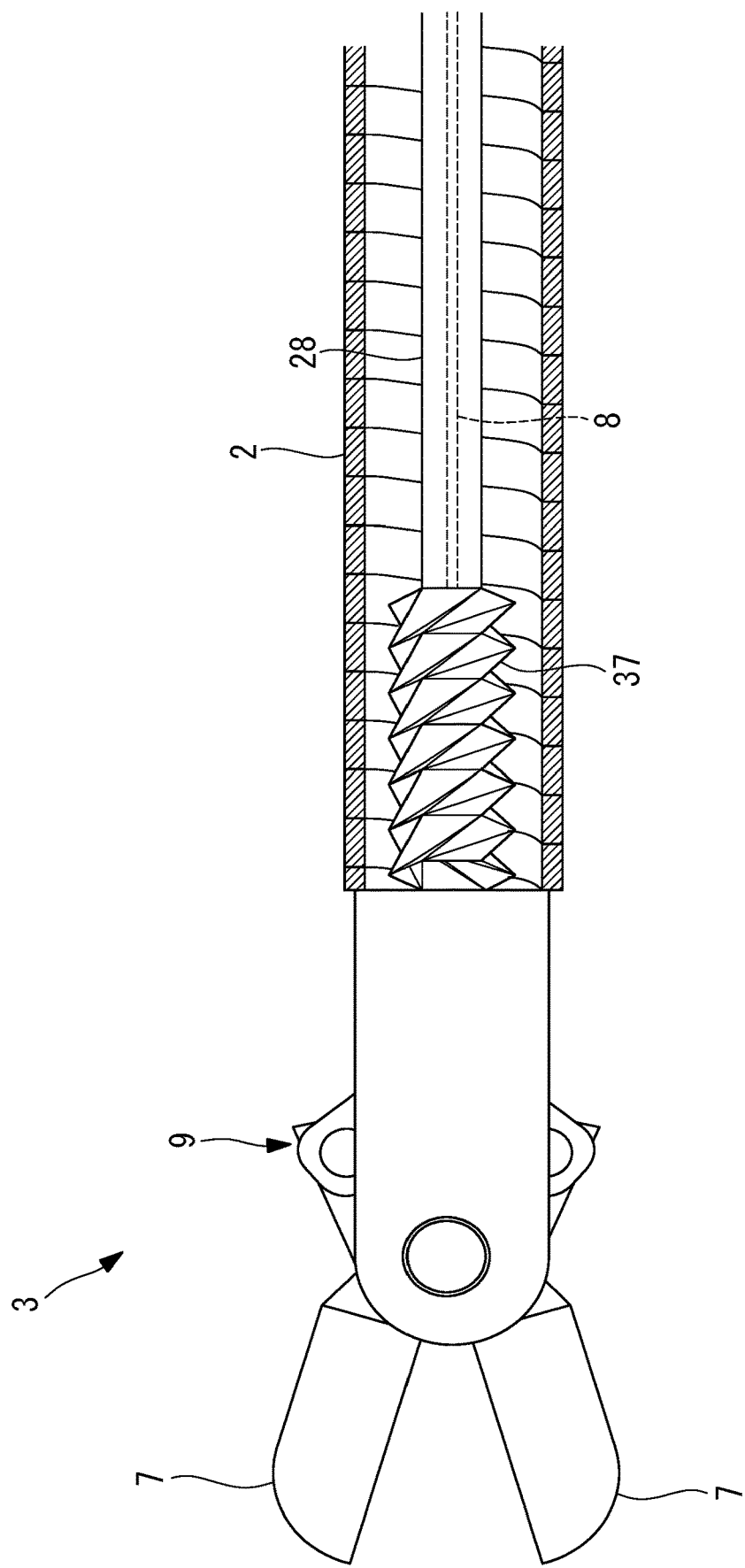
FIG. 20 is a partial vertical sectional view of the vicinity of the operating portion illustrating another modification of the treatment tool in FIG. 1.

In addition, instead of the twisting wire 5 for converting the input tension into a rotational force, as illustrated in FIG. 20, a cylindrical body 37 having a cylindrical torsional folding structure as used in origami engineering may be adopted.

The cylindrical body 37 is configured to twist around the longitudinal axis at both ends in the longitudinal axis direction in the process of contraction in the longitudinal axis direction, and to untwist in the process of extension. Accordingly, an extension/contraction force input at the proximal end can also be converted into rotation about the longitudinal axis at the front end by the cylindrical body 37.

Figure 21:
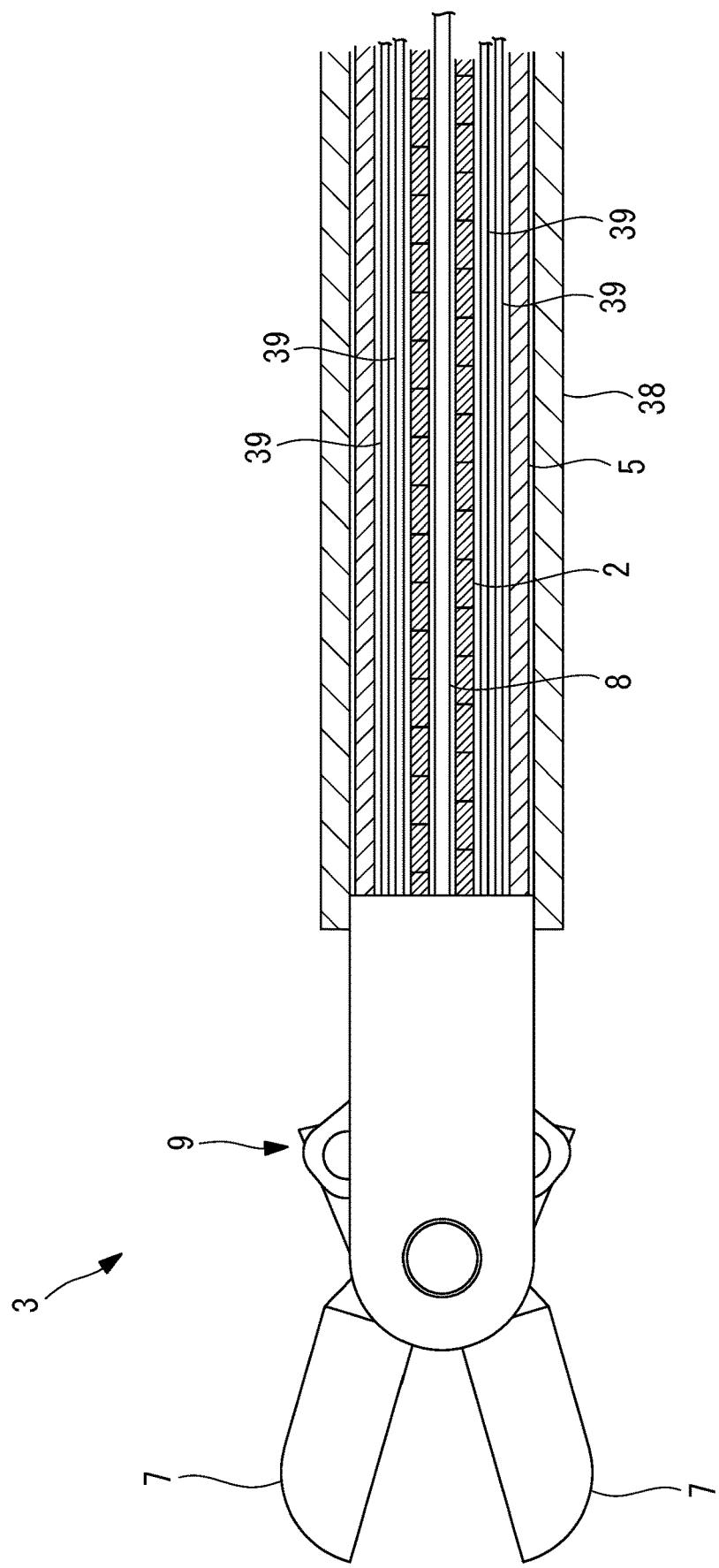
FIG. 21 is a partial vertical sectional view of the vicinity of the operating portion illustrating another modification of the treatment tool in FIG. 1.
Figure 22:
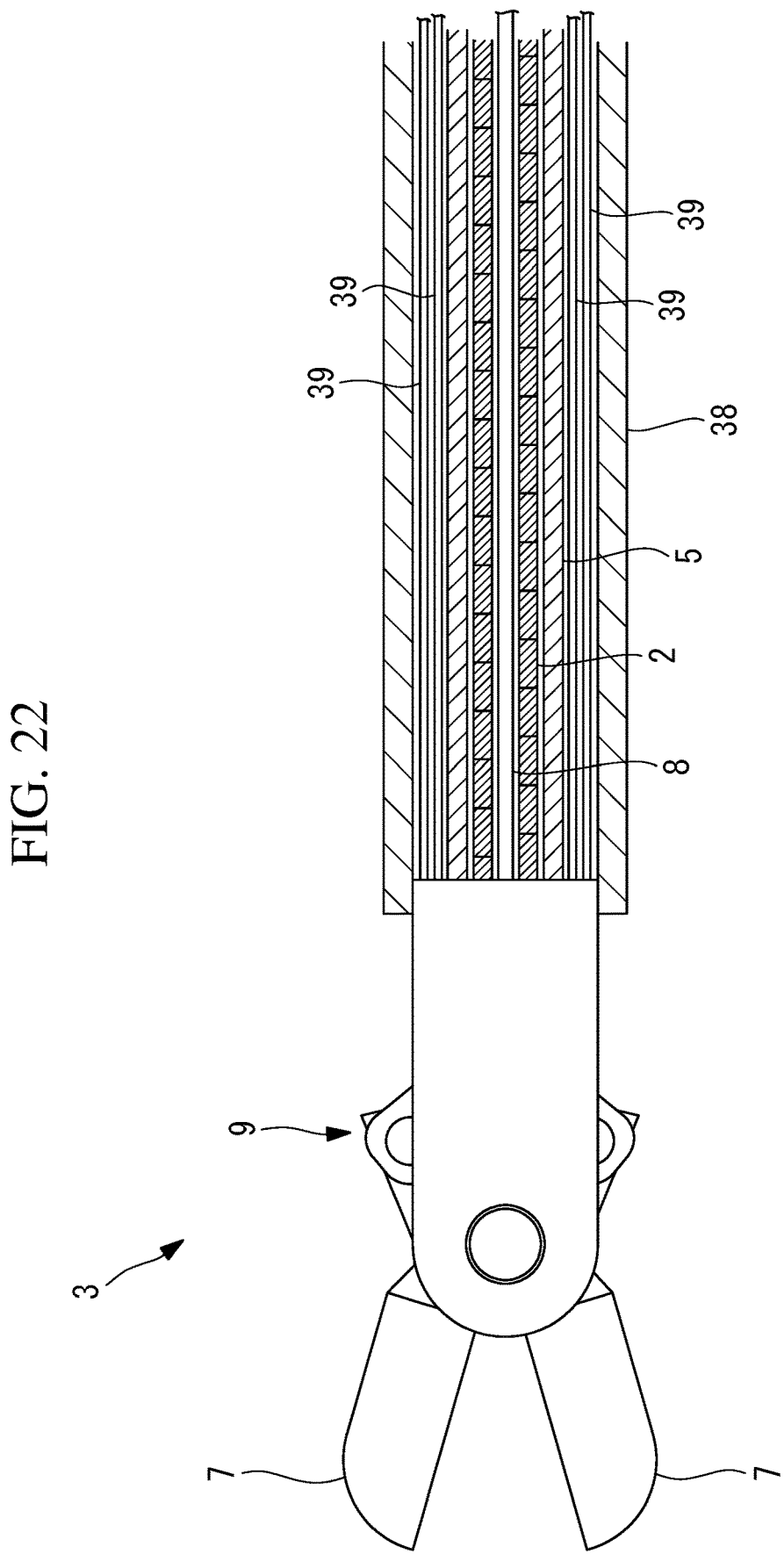
FIG. 22 is a partial vertical sectional view of the vicinity of the operating portion illustrating a modification of the treatment tool in FIG. 21.

In addition, in the present embodiment, an example in which the twisting wire 5 is disposed inside the coil sheath 2 has been described; however, instead of this, as illustrated in FIGS. 21 and 22, the tubular twisting wire 5 may be disposed radially outside the coil sheath 2. In the example illustrated in the figure, a covering 38 composed of a flexible material is disposed outside the twisting wire 5. In FIG. 22, a lead wire 39 leading to the gripper 3 is disposed between the covering 38 and the twisting wire 5, and in FIG. 21, the lead wire 39 is disposed between the twisting wire 5 and the coil sheath 2.

The above-described embodiment also leads to the following aspects.

According to an aspect of the present invention, a treatment tool includes an elongated long member, a treatment portion supported at a distal end of the long member so as to be rotatable about a longitudinal axis of the long member, an operating portion disposed at a proximal end of the long member and operated by an operator, a motive-force transmission member that connects the operating portion and the treatment portion to each other and that transmits a motive force input at the operating portion to the treatment portion, in which the operating portion includes an operating portion body fixed to the long member, a movable operating member movably supported with respect to the operating portion body, and a connection portion that is disposed between the movable operating member and the operating portion body, that allows the movement of the movable operating member with respect to the operating portion body by causing the movable operating member to be separated from the operating portion body and that locks the movable operating member so as not to move with respect to the operating portion body due to a resistance generated therebetween by causing the movable operating member and the operating portion body to be close to each other.

According to this aspect, when the operator operates the operating portion and inputs a motive force, by moving the movable operating member away from the operating portion body at the connection portion and inputting a motive force to the movable operating member in this state, the input motive force is transmitted to the treatment portion by the motive-force transmission member, and the treatment portion is rotated about the longitudinal axis of the long member. Then, after the treatment portion has been rotated to a desired angular position, the movable operating member is brought close to the operating portion body at the connection portion, and locked so that the movable operating member does not move with respect to the operating portion body due to a resistance therebetween. Consequently, even if an external force acts on the treatment portion, the angular position is maintained.

Since the movable operating member operated by the operator can be switched between relative movement between the movable operating member and the operating portion body simply by moving the movable operating member close to or away from the operating portion body, a large-scale mechanism such as one including a brake rotor and a brake shoe is not required, an increase in the size of the operating portion can be prevented, and cost can be reduced.

In the above aspect, the operating portion may input a tension to the motive-force transmission member as the motive force, and the motive-force transmission member may convert the input tension into a rotational force and transmit the rotational force to the treatment portion.

Thus, by moving the movable operating member with respect to the operating portion body and inputting a tension to the motive-force transmission member, the input tension is converted into a rotational force by the motive-force transmission member, and the treatment portion can be rotated about the longitudinal axis at the distal end of the long member.

In addition, in the above aspect, the resistance at the connection portion may be a frictional resistance.

Thus, the movable operating member can be brought into contact with the operating portion body by bringing the movable operating member close to the operating portion body, and can be locked so that the two do not move relative to each other due to a frictional resistance. In addition, by causing the movable operating member to be separated from the operating portion body, the frictional resistance between the two can be eliminated, and relative movement between the two is enabled.

In addition, in the above aspect, the treatment tool may further include an urging means that urges the movable operating member in a direction approaching the operating portion body at the connection portion.

Thus, with the operator applying a force to the movable operating member and separating the movable operating member from the operating portion body, the treatment portion can be rotated at the distal end of the long member by the application of a motive force to the movable operating member, and, by releasing the force applied to the movable operating member by the operator, the movable operating member can be moved by the urging means in a direction approaching the operating portion body, resistance can be generated between the movable operating member and the operating portion body, and the movable operating member and the operating portion body can be locked in such a manner that they do not move relative to each other.

In addition, in the above aspect, the connection portion may undergo processing for increasing a friction coefficient.

Thus, when the movable operating member and the operating portion body are brought into contact with each other, a large frictional resistance can be generated due to the friction coefficient increased by the processing, and locking can be performed more reliably so that the movable operating member and the operating portion body do not move relative to each other.

In addition, in the above aspect, a direction in which the tension is input to the motive-force transmission member may be the same as a direction in which the movable operating member and the operating portion body approach or separate from each other at the connection portion.

Thus, if the movable operating member is moved in a direction away from the operating portion body, the movable operating member is urged in a direction toward the operating portion body by the tension input to the motive-force transmission member. Consequently, the motive-force transmission member can be used as an urging means, and the configuration can be simplified.

In addition, in the above aspect, the urging means may be an elastic member.

Thus, since the movable operating member is urged in a direction toward the operating portion body by an elastic force of an elastic member, an urging means can be easily formed.

In addition, in the above aspect, the urging means may include a magnet member disposed on at least one of the movable operating member and the operating portion body, and a magnetic member that is disposed on the other of the movable operating member and the operating portion body and that urges the movable operating member and the operating portion body in directions toward each other by a magnetic force between the magnet member and the magnetic member.

Thus, with the magnetic force generated between the magnet member disposed on at least one of the movable operating member and the operating portion body and the magnetic member disposed on the other of the movable operating member and the operating portion body, the movable operating member can be urged in a direction toward the operating portion body, and the movable operating member and the operating portion body can be locked so as not to move relative to each other.

REFERENCE SIGNS LIST 1 treatment tool
2 coil sheath (long member)
3 gripper (treatment portion)
4 operating portion
5 twisting wire (motive-force transmission member)
10 operating portion body
11 dial (movable operating member)
15 contact portion (connection portion)
16, 24, 27 spring (urging means, elastic member)
17, 18 irregularities (connection portion)
19 magnet (magnet member)
20 magnetic member
25, 33 operation piece (movable operating member)
28 shaft (motive-force transmission member)
30 wire (motive-force transmission member)

The invention claimed is:

1. A treatment tool comprising:
an elongated member;
an end effector supported at a distal end of the elongated member so as to be rotatable about a longitudinal axis of the elongated member;
a twisting wire, a first end of the twisting wire being connected to the end effector, a second end of the twisting wire extending toward a proximal end side of the elongated member through an inside of the elongated member;
a handle disposed at the proximal end side of the elongated member, the handle being fixed to the elongated member;
a movable body movable relative to the handle between:
a first state where a first surface of the movable body contacts a second surface of the handle to restrict rotation of the end effector about the longitudinal axis of the elongated member; and
a second state where the first surface is moved away from contact with the second surface to permit rotation of the end effector about the longitudinal axis of the elongated member; and
a converting mechanism configured to couple the movable body with the twisting wire such that:
when the movable body is moved into the second state, the movable body applies a tensile force to the twisting wire; and
when the movable body is released from the second state, the movable body is urged in a direction toward a distal end side of the elongated member by at least a restoring force of the twisting wire to move the movable body into the first state;
wherein the movable body is a dial movable in rotation such that the rotation of the dial results in moving the dial in a longitudinal axis direction of the elongated member, and the converting mechanism comprises a portion of the twisting wire having a male thread, and the dial having a female thread matingly engaged with the male thread.

2. The treatment tool according to claim 1, wherein the first surface is configured to prevent the rotation of the dial by a friction force.

3. The treatment tool according to claim 1, wherein the movable body is configured to be passively urged toward the distal end side of the elongated member by the restoring force of the twisting wire when the movable body is not operated by the operator.

4. The treatment tool according to claim 1, wherein the twisting wire is configured to rotate around the longitudinal axis of the elongated member to apply the tensile force and to rotate the end effector around the longitudinal axis of the elongated member.

5. The treatment tool according to claim 1, wherein a coefficient of friction between the first and second surfaces is greater than a coefficient of friction between the first surface and surfaces of the handle other than the second surface.

6. The treatment tool according to claim 1, further comprising a biasing spring for biasing the first surface towards the second surface.

7. A treatment tool comprising:
a tube having a distal end configured to rotatably support an end effector;
a twisting wire disposed along a longitudinal axis of the tube, the twisting wire having a distal end and a proximal end, the end effector being connected to the distal end of the twisting wire; and
at least one wire movable in a longitudinal direction to actuate the end effector, the at least one wire actuating the end effector separately from rotation of the twisting wire to rotate the treatment tool,
a handle disposed at a proximal end side of the tube, and
a dial disposed at the handle and having a locked position and an unlocked position, the dial being configured to rotate around the longitudinal axis of the tube and to move along a longitudinal axis direction upon rotation of the dial,
wherein the handle includes a contact surface configured to contact with a distal end surface of the dial to prevent the rotation of the dial,
in the unlocked position, the distal end surface of the dial moves proximally from the contact surface to apply a tensile force to the twisting wire,
in the locked position, the distal end surface of the dial contacts with the contact surface due to at least a restoring force of the twisting wire;
a converting mechanism comprising: a male thread disposed on the tube and fixed to a portion of the twisting wire, the male thread being disposed along the longitudinal axis direction of the tube; and a female thread disposed on the dial and configured to matingly engage with the male thread, the female thread being disposed along the longitudinal axis of the tube; and the dial is movable in rotation such that the rotation of the dial results in moving the dial in the longitudinal axis direction of the tube.

8. The treatment tool according to claim 7, wherein a coefficient of friction between the contact surface and the distal end surface is greater than a coefficient of friction between the distal end surface and surfaces of the handle other than the contact surface.

9. The treatment tool according to claim 7, further comprising a biasing spring for biasing the dial towards the contact surface.

10. A treatment tool comprising:
an elongated member;
an end effector supported at a distal end of the elongated member so as to be rotatable about a longitudinal axis of the elongated member;
a twisting wire, a first end of the twisting wire being connected to the end effector, a second end of the twisting wire extending toward a proximal end side of the elongated member through an inside of the elongated member;
a handle disposed at the proximal end side of the elongated member, the handle being fixed to the elongated member;
a dial rotatably movable relative to the handle between:
a first state where a first surface of the dial contacts a second surface of the handle to restrict rotation of the end effector about the longitudinal axis of the elongated member; and
a second state where the first surface is moved away from contact with the second surface to permit rotation of the end effector about the longitudinal axis of the elongated member; and
a converting mechanism configured to couple the dial with the twisting wire such that:
when the dial is rotated to move into the second state, the dial applies a tensile force to the twisting wire;
when the dial is released from the second state, the dial is urged to move in translation in a longitudinal axis direction toward a distal end side of the elongated member by at least a restoring force of the twisting wire to move dial into the first state;
wherein the converting mechanism comprises:
a portion of the twisting wire having a male thread, and the dial having a female thread matingly engaged with the male thread; and
the dial is movable in rotation such that the rotation of the dial results in moving the dial in the longitudinal axis direction of the elongated member.

11. The treatment tool according to claim 10, wherein the first surface is configured to prevent the rotation of the dial by a friction force.

12. The treatment tool according to claim 11, wherein the friction force disappears by moving the dial along the longitudinal axis direction toward the proximal end side of the elongated member such that the second surface is separated from the first surface.

13. The treatment tool according to claim 10, wherein the dial is configured to be urged toward the distal end side of the elongated member by the restoring force of the twisting wire passively when the dial is not operated by the operator.

14. The treatment tool according to claim 10, wherein the twisting wire is configured to rotate around the longitudinal axis of the elongated member to apply the tensile force and to rotate the end effector around the longitudinal axis of the elongated member.

15. The treatment tool according to claim 10, wherein a coefficient of friction between the first and second surfaces is greater than a coefficient of friction between the first surface and surfaces of the handle other than the second surface.

16. The treatment tool according to claim 10, further comprising a biasing spring for biasing the first surface towards the second surface.

* * * * *